Figure 1:
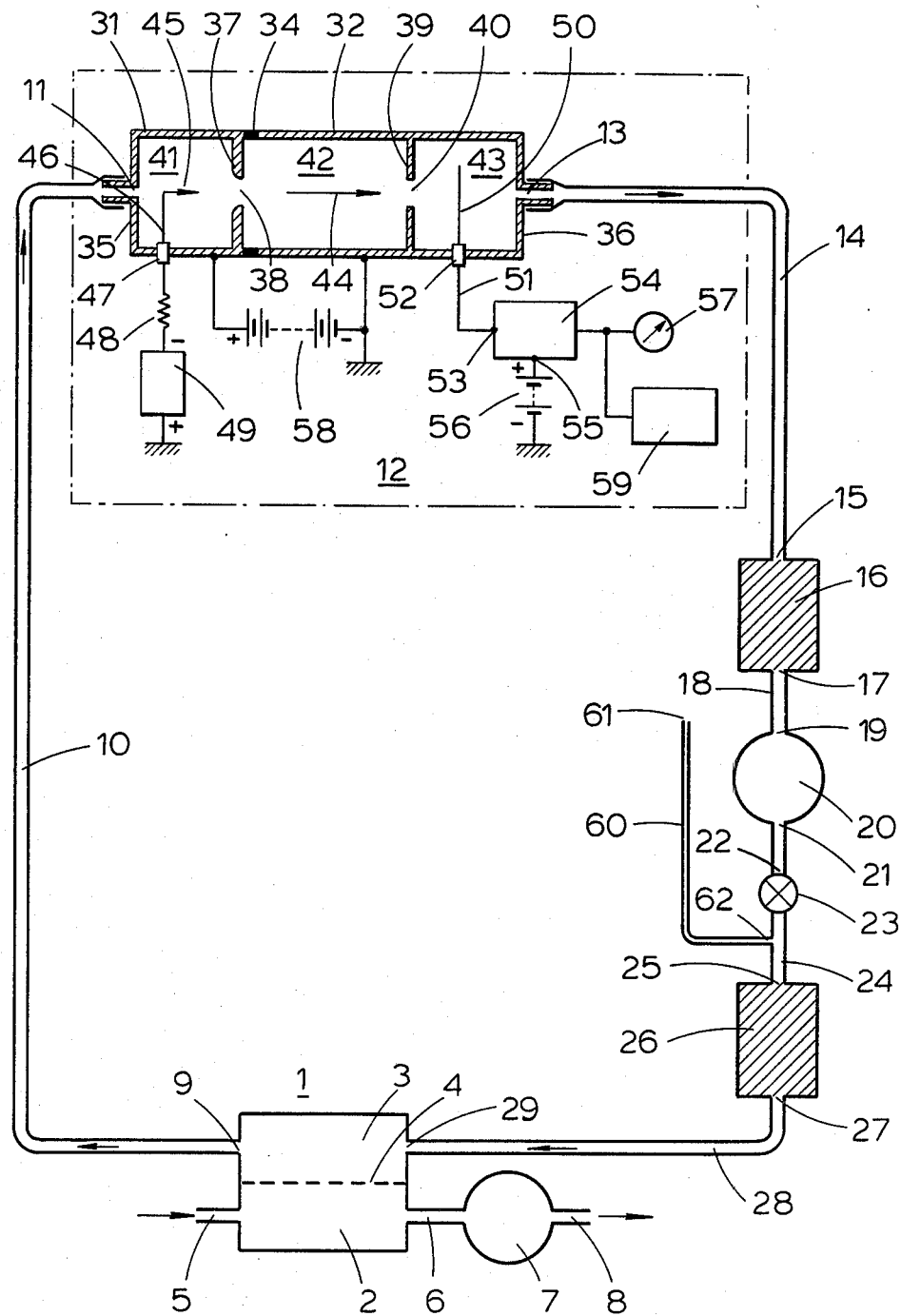

United States Patent [19]

Bradshaw et al.

[11] 4,317,995

[45] Mar. 2, 1982

[54] TRACE VAPOR DETECTOR

[75] Inventors: Robert F. D. Bradshaw, Markyate; John L. Brokenshire, Amersham, both of England

[73] Assignee: U.S. Philips Corp., New York, N.Y.

[21] Appl. No.: 151,219

[22] Filed: May 19, 1980

[30] Foreign Application Priority Data

Jun. 21, 1979 [GB] United Kingdom ............... 21678/79

[51] Int. Cl.³ .......................... B01D 59/44; H01J 49/00
[52] U.S. Cl. ..................................... 250/288; 250/286; 250/309
[58] Field of Search ................. 250/288, 309, 286, 287

[56] References Cited

U.S. PATENT DOCUMENTS 3,629,574 12/1971 Carroll ................................. 250/287
3,668,382 6/1972 Cohen et al. .......................... 250/288
4,239,967 12/1980 Carr et al. ............................ 250/288

Primary Examiner—Harold A. Dixon
Attorney, Agent, or Firm—Paul R. Miller

[57] ABSTRACT

A detector for trace quantities of chemical species in the atmosphere includes a pump for drawing an atmospheric sample through transfer means which transfer species molecules present in the sample to a dry carrier gas circulating in a closed gas flow circuit including the transfer means, an ionmobility type detector, filters and a circulating pump; the filters remove water molecules and species molecules from the carrier gas. The carrier gas may be air. The arrangement inhibits water vapor reaching the detector and reducing its sensitivity to the chemical species.

11 Claims, 2 Drawing Figures

TRACE VAPOR DETECTOR

The present invention relates to apparatus for detecting trace quantities of chemical species in a gaseous mixture by drawing the gaseous mixture through a hollow body, said hollow body having serially arranged an inlet, a first, a second and a third internal region and an outlet, the first region containing means for ionising a proportion of the molecules of the gaseous mixture including molecules of the chemical species and means for selecting ions of one polarity for travel with the gaseous mixture into the second region, means for promoting the flow of the gaseous mixture through the second region as a jet of substantially uniform velocity, means for producing in the second region an electric field which urges ions of the selected polarity in a direction opposite to that of the gas flow and means in the third region for collecting ions of the selected polarity, the arrangement being such that, in operation, ions of the selected polarity whose ionic mobilities exceed a value dependent on the strength of the said electric field and the velocity of the gas flow can be prevented from entering the third region.

The expression "chemical species" relates to vapour molecules of substances which are capable of forming relatively stable ions in the presence of oxygen, said ions of the chemical species having a mobility which is low compared with the mobility of ions which may be formed from other constituents of the gaseous mixture.

Apparatus of the type hereinbefore specified is described and claimed in our European patent application No 79200128.1 and is manufactured by our associated company Pye Dynamics Limited under the Type No. PD3.

The known apparatus has high sensitivity to chemical species of the type hereinbefore specified when present in trace quantities in a dry gaseous mixture. It is found however, that for some such species, the sensitivity may be reduced if water vapour is present in the gaseous mixture. For example, the known apparatus has high sensitivity to each of the chemically similar substances 1, 2-ethanediol dinitrate and 1, 2, 3-propanetriol trinitrate in the absence of water vapour. The presence of water vapour has negligible effect on its sensitivity to 1, 2, 3-propanetriol trinitrate but substantially reduces its sensitivity to 1, 2-ethanediol dinitrate. The presence of water vapour in the gaseous mixture is found to produce a similar reduction in the sensitivity of the known apparatus to certain other chemical species. Since water vapour is a normal constituent of the atmosphere, this effect restricts the capacity of the known apparatus to detect such water-sensitive chemical species when present in trace quantities in the atmosphere.

The effect is believed to arise in the following manner. In the apparatus, a proportion of the molecules of the mixture are ionised in the first region by e.g. a corona discharge. Relatively few molecules of the chemical species, which are present in the mixture only in very low concentration, are directly ionised in this way. However a primary ion population is formed by ionisation of molecules, e.g. air molecules, which are present in the mixture in massive numbers. Charge exchange reactions then occur between these primary (air) ions and species molecules, resulting in a substantial proportion of the species molecules present becoming ionised. It is believed that in the case of 1, 2-ethanediol dinitrate and other water-sensitive species, the presence of water molecules and/or ions produced therefrom interferes to a greater or less extent with these reactions.

U.S. Pat. No. 3,668,382 discloses a method of detecting trace material in a gaseous sample containing moisture which method includes diluting the gaseous sample by adding to it a dry gas prior to detection, but states that such dilution reduces sensitivity.

It is an object of the present invention to provide means whereby the sensitivity of the known apparatus may be rendered substantially independent of the presence of water vapour.

According to the invention apparatus for detecting trace quantities of chemical species in a gaseous mixture by drawing the gaseous mixture through a hollow body, said hollow body having serially arranged an inlet, a first, a second and a third internal region and an outlet, the first region containing means for ionising a proportion of the molecules of the gaseous mixture including molecules of the chemical species and means for selecting ions of one polarity for travel with the gaseous mixture into the second region, means for promoting the flow of the gaseous mixture through the second region as a jet of substantially uniform velocity, means for producing in the second region an electric field which urges ions of the selected polarity in a direction opposite that of the gas flow and means in the third region for collecting ions of the selected polarity, the arrangement being such that, in operation, ions of the selected polarity whose ionic mobilities exceed a value dependent on the strength of the electric field and the velocity of the gas flow can be prevented from entering the third region is characterised by means for transferring molecules of the chemical species from the atmosphere to a dry gaseous mixture drawn through the hollow body.

According to one aspect of the invention, the transfer means comprises a first chamber having an inlet connected to a source of the dry gaseous mixture and an outlet connected to the inlet of the hollow body, a second chamber having an inlet open to the atmosphere and an outlet connected to pump means for drawing atmospheric air through the second chamber, the first and second chambers being separated by a partition permeable to molecules of the chemical species and substantially impermeable to water molecules.

The partition may be a membrane of a silicone rubber composition.

According to another aspect of the invention the transfer means comprises an elongate chamber having a first port adjacent its one end and a second port adjacent its other end, the chamber containing a filament effective to adsorb molecules of the chemical species when cold and to desorb the molecules when heated, valve means effective in a first position to connect the first port to atmosphere and the second port to pump means for drawing atmospheric air through the chamber and effective in a second position to connect the first port to the inlet of the hollow body and the second port to the source of the dry gaseous mixture, and means for heating the filament when the valve means is in its second position.

The apparatus may be further characterised by a gas flow circuit such that the dry gaseous mixture, after passing in turn through the transfer means and the hollow body is passed through at least one filter unit of a type effective to remove from the mixture molecules of the chemical species and water molecules and is returned to the transfer means. A first filter unit, a pump for circulating the gaseous mixture round the said gas flow circuit, a flow rate control valve and a second filter unit may be connected in series between the outlet of the hollow body and the transfer means.

The dry gaseous mixture may be dry air or it may be an inert carrier gas or a mixture of inert gases.

Figure 2:
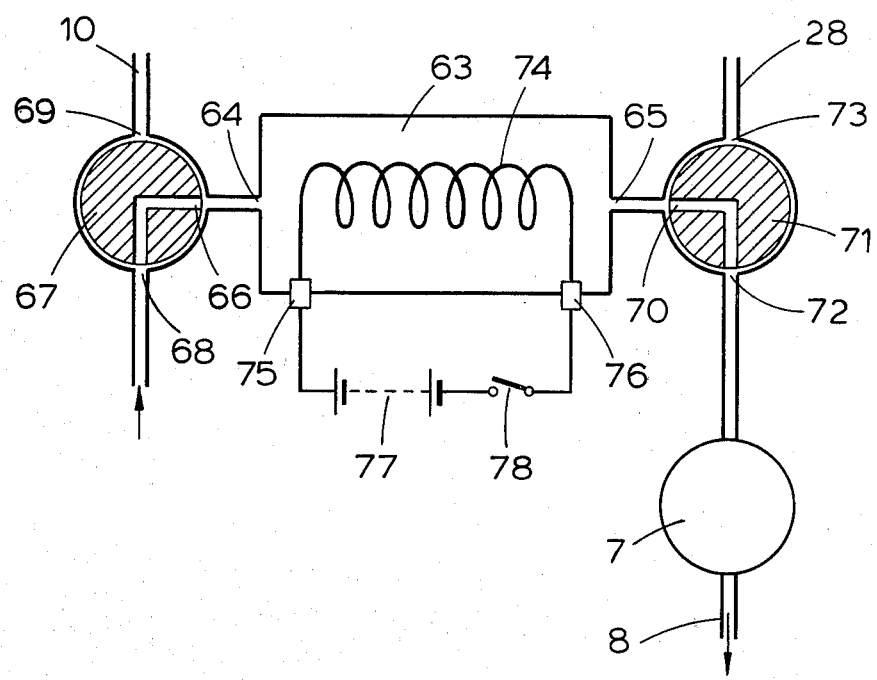

Embodiments of the invention will now be described, by way of example, with reference to the attached drawings, of which:

FIG. 1 is a schematic diagram of trace vapour detection apparatus embodying the invention, and FIG. 2 is a schematic diagram of a separator unit alternative to the separator unit of FIG. 1.

Referring first to FIG. 1, transfer means 1 comprises a first chamber 2 and a second chamber 3, separated by a semi-permeable membrane 4. The semi-permeable membrane 4 may comprise sheet of a silicone-based rubber material such as a di-methyl silicone rubber supplied by Esco Rubber Limited which has a low transmission for the basic constituents of air, e.g. oxygen, nitrogen, carbon dioxide, argon and water, but a high transmission for vapours of chemical species of the type specified hereinbefore.

The chamber 2 has an inlet 5 open to the atmosphere and an outlet 6 connected to a pump 7 effective in operation to draw atmosphere air through the chamber 2 and to exhaust said air to atmosphere through an exhaust port 8. A proportion of the molecules of chemical species contained in the air drawn through the chamber 2 pass through the membrane 4 into the chamber 3.

The chamber 3 has an outlet 9 which is connected via a tube 10 to an inlet 11 of a trace vapour detector shown generally within the broken rectangle 12. The detector 12 has an outlet 13 connected via a tube 14 to an inlet 15 of a first filter unit 16 having an outlet 17.

The outlet 17 of the filter unit 16 is connected via a tube 18 to an inlet 19 of a further pump 20. An outlet 21 of the pump 20 is connected via a tube 22, a flow control valve 23 and a tube 24 to an inlet 25 of a second filter unit 26. An outlet 27 of the filter unit 26 is connected via a tube 28 to an inlet 29 of the chamber 3 of the separation unit 1.

There is thus provided a closed circuit including the chamber 3, the detector 12, the first filter unit 16 and the second filter unit 26 around which air may be continuously circulated by operation of the pump 20, the rate of flow of the circulating air being controllable by adjustment of the valve 23.

The first filter unit 16 and the second filter unit 26 may be similar and may comprise respective chambers packed with a porous material effective to remove water vapour and other impurities, including molecules of the chemical species from the circulating air. A suitable material is Molecular Sieve 5A. The filter units 16 and 26 additionally serve to prevent pulsations in the air flow, which may be produced by the operation of the pump 20, being transmitted to the detector unit 12.

Molecules of the chemical species which pass through the membrane 4 are entrained in the flow of dry air passing through the chamber 3 and are carried thereby to the detector 12, which may be of the type described more fully in our European patent application No. 79200128.1. (U.K. Applications Nos. 23040/78 and 24764/78).

Briefly, the detector 12 may comprise a generally cylindrical body formed by co-axial tubes 31 and 32 of electrically conductive material such as copper or aluminium joined in end to end relationship by a ring 34 of insulating material. The tube 31 is provided at its free end with an end-wall 35 of conductive material having the inlet 11 located centrally thereof. Similarly the tube 32 is provided at its free end with an electrically-conductive end wall 36 having the outlet 13 located centrally thereof.

At the end of the tube 31 adjacent the tube 32 is provided a septum 37 comprising a metal disc having an axial aperture 38, the septum 37 being electrically connected to the wall of the tube 31.

A baffle 39 is located at a point intermediate the ends of the tube 32, said baffle comprising a metallic disc having at least one aperture 40 therein, a sheet of metallic gauze or a metallic grid-like structure, the baffle being electrically connected to the wall of the tube 32.

Air circulated by the pump 20 enters the detector 12 at the inlet 11, passes successively through a first region 41 defined by the end wall 35 and the septum 37, a second region 42 defined by the septum 37 and the baffle 39, a third region 43 defined by the baffle 39 and the end wall 36 and leaves the detector through the outlet 13.

The aperture 38 in the septum 37 is profiled so that the air flow passes through the region 42 as a smooth jet of substantially uniform velocity, as indicated by the arrow 44. In an alternative arrangement the septum 9 may be provided with a plurality of apertures, each regularly profiled so that the air flow passes through the region 42 as a corresponding plurality of smooth jets of uniform velocity.

Within the region 41, a pointed electrode 45 is supported by a lead 46 which passes through an insulator 47 mounted in the wall of the tube 31. Outside the tube 31, the lead 46 is connected, preferably via a resistor 48, to one terminal of a high voltage supply unit 49 whose other terminal is connected to ground. The unit 49 produces a potential V1, typically 3000 V, sufficient to produce a corona discharge from the electrode 45. The value of the resistor 48 may be selected so that the current $I_D$ of the corona discharge is less than 100 nanoamps and preferably less than 30 nanoamps.

The discharge ionises at least a proportion of the molecules present in the air flow in massive numbers. Initially, a bi-polar ion population is produced, but the high potential of the electrode relative to the tube 31 and the resulting intense electric field in its vicinity causes ions of one polarity to migrate to the electrode 45, where they are neutralised. Thus a primary ion population of the opposite polarity travels with the gas flow towards the aperture 38 of the septum 37. If the electrode 45 is negative with respect to the tube 31, as shown in FIG. 1, a primary population of negative ions is produced.

During the travel of the primary ion population towards the septum, charge exchange reactions take place between primary ions and molecules of the chemical species present in the air flow. Since any water vapour which may originally have been present in the circulating air has been removed by the filters 16 and 26, there are no water molecules or ions produced therefrom available to interfere with the reactions if the chemical species is water-sensitive. Thus there arrives at the aperture 38 a mixture of primary ions and secondary ions of the chemical species, all the ions being of the one selected polarity, i.e. of negative polarity for the arrangement of FIG. 1.

In the absence of an electric field in the region 42, substantially all the ions arriving at the aperture 38 are carried by the jet flow 44 across the region and through the aperture 40 of the baffle 39 into the region 43. In the region 43 is provided an electrode 50, which may be a wire, a plate or a grid, supported by a lead 51 which passes through an insulator 52 in the wall of the tube 32. Outside the tube, the lead 51 is connected to an input terminal 53 of a current amplifier unit 54. A common terminal 55 of the unit 54 is connected to a point of relatively low potential V2, for example 5 volts, with respect to the wall of the tube 31, which is itself connected to ground, as indicated schematically in FIG. 1 by the battery 56. The electrode 50 is therefore held at the potential V2, whose polarity is such that ions arriving in the region 43 are attracted to the electrode, producing a current input to the amplifier unit 54. The corresponding output current of the unit may be observed on a meter 57. For negative ions, the battery 56 is connected so that the electrode 50 is held positive with respect to the tube 32.

A source of potential V3, typically 300 volts, indicated schematically in FIG. 1 by the battery 58, is connected between the wall of the tube 32 and the wall of the tube 31, so that for negative ions, the tube 31 and with it the septum 37 is positive with respect to the tube 32 and in particular to the baffle 39. An electric field is therefore produced in the region 42. Although there are fringing effects adjacent the wall of the tube 32, the field in the vicinity of the jet 44 is substantially parallel to the axis of the jet and is effective to urge negative ions in a direction opposite to that of the gas flow.

The strength of the electric field in the vicinity of the jet 44 is determined by the separation between the septum 37 and the baffle 39 and by the potential V3 of the source 58. For a given field strength, ions whose ionic mobilities have a certain critical value will be driven by the field at exactly the velocity of the jet flow, but in the opposite direction. Such ions will remain stationary so far as motion parallel to the jet axis is concerned. Their random transverse motion may move them laterally into a region of slower gas flow and the field in this region may then drive them back to the septum 9. Consequently such ions are substantially prevented by the field from reaching the baffle 39 and entering the region 43. A fortiori, ions with mobilities greater than the critical value are prevented from entering the region 43.

Ions with mobilities lower than the critical value are given a velocity by the field in the region 42 lower than the velocity of the jet flow. Although some such ions may be carried by random transverse motions into regions where the velocity of the gas flow is less than the velocity imparted to them by the field, in general ions whose mobilities are less than the critical value will be carried by the jet flow through the region 42, albeit at a velocity less than that of the jet flow, and will enter the region 43 and be collected by the electrode 50.

Thus, for a given field strength and jet flow rate in the region 42, ions with mobilities equal to or exceeding a critical value have no possibility of reaching the electrode 50. For ions with mobilities less than the critical value there is a finite possibility which increases as the mobility of the ion, and hence the time taken for it to traverse the region 42, decreases.

In use the jet flow rate is set to a convenient value, typically in the range 300 to 400 cm per second by means of the flow control valve 23 and the potential V3 of the source 58 is set to produce a field strength in the region 42 such as to exclude substantially all the primary (air) ions from the region 43 but to allow heavier, less mobile ions such as the secondary ions produced from chemical species of the type specified to enter the region and reach the collector electrode 50. Such ions manifest themselves as an increase in the output current of the amplifier unit 54 which may be observed on the meter 57.

If the atmospheric air drawn through the chamber 2 of the transfer means 1 does not contain the chemical species, it is apparent that no species molecules will be present in the air flow entering the detector unit 12. The amplifier unit 54 will then produce a substantially constant low output current (background current) which is indicated by the meter 57. If desired the meter may be offset, either mechanically or electrically, to give a zero reading under these conditions.

When atmospheric air including trace quantities of chemical species of the type specified is drawn through the chamber 2, species molecules become entrained in the dry air flow to the detector, and the meter reading increases by an amount dependent on the concentration of the particular species.

An alarm unit 59 may be provided having its input connected to the output of the amplifier unit 54 and arranged to produce an audible and/or visual alarm signal if the output current of the amplifier unit exceeds a threshold level which is greater than the background current level.

The detector unit 12 as described with reference to FIG. 1 is adapted to detect the presence of chemical species which will form negative ions by charge exchange reactions. To adapt the unit 12 to detect species which will form positive ions, it is necessary merely to reverse the polarity of the high voltage supply unit 49 and the polarities of the voltage 56 and 58.

Heating means, not shown in FIG. 1, may be provided to raise the temperature of the transfer means 1, and in particular the temperature of the membrane 4 above ambient temperature. Such means may conveniently comprise an electric heating element wrapped around and electrically insulated from the outer surface of the unit 1. Means may be provided for controlling a supply of electric current to the element so as to maintain the temperature substantially at a desired value.

Similarly, heating means may be provided for maintaining the detector unit 12 at a desired temperature greater than ambient temperature, conveniently comprising an electric heating element wrapped around and electrically insulated from the outer surfaces of the tubes 31 and 32, together with means for controlling the supply of current to the element so as to maintain the temperature of the detector unit at a desired value. Preferably the temperature of the separator unit 1 and the detector unit 12 are independently controllable.

To prevent any change of pressure within the closed gas flow circuit due either to changes of ambient temperature or to heating of the separator unit and/or the detector unit, a vent may be provided. The vent may conveniently comprise a length of capillary tube 60 having its one end 61 open to atmosphere and its other end 62 connected into the tube 24, so as to ensure that any water vapour which may enter through the vent is removed from the circulating gas flow by the filter 26 and does not reach the detector unit 12.

In the embodiment described hereinabove, species molecules are transported from the separator unit 1 to the detector unit 12 by air flowing in a closed-loop circulatory system from which any water vapour is removed by the filters 16 and 26. If desired an inert gas or mixture of inert gases may be employed instead of air in the closed-loop system. By inert gas is meant a gas which is non-reactive with the chemical species. Suitable gases include, for example nitrogen, argon and helium. Preferably a supply of the dry gas or mixture of gases is connected to the closed-loop system at a point between the outlet 27 of the filter unit 26 and the inlet 29 of the separator unit 1, so as to compensate for loss of gas through the vent 60. The outward flow of the gas through the vent prevents ingress of air which might otherwise contaminate the carrier gas circulating in the closed system.

There will now be described with reference to FIG. 2 a further separator unit suitable for use in apparatus according to the present invention.

Referring to FIG. 2, the transfer means comprises a chamber 63, generally of closed cylindrical form having a port 64 in its one end-wall and a port 65 in its other end wall. The port 64 is connected to a common port 66 of a first two-way gas flow valve 67 such that the common port 66 may optionally be connected to a port 68 or to a further port 69. The port 68 of the valve 67 is connected to atmosphere and the port 69 to the tube 10 (see FIG. 1).

The port 65 of the chamber 63 is connected to a common port 70 of a second two-way gas flow valve 71 such that the common port 70 may optionally be connected to a port 72 or to a further port 73. The port 72 is connected to the inlet of the pump 7 and the port 73 is connected to the tube 28.

The valves 67 and 71 are preferably mechanically connected for simultaneous movement between a first position as shown in FIG. 2 wherein the ports 64 and 65 of the chamber 63 are connected respectively to atmosphere and to the pump 7, and a second position wherein the ports 64 and 65 are connected respectively to the tube 10 and the tube 28.

Within the chamber 63 is mounted a filament 74 of a substance which adsorbs molecules of chemical species of the type specified when cold and desorbs the molecules when heated. Suitable filaments are electrically conductive wires with a high surface reactivity such as platinum, palladium, chromium and nickel, and alloys thereof. The surface of the filament may be treated to increase its capacity to adsorb the chemical species and subsequently to desorb the species when the filament is heated, e.g. by the passage of an electric current therethrough.

The ends of the filament pass through respective insulators 75 and 76 in the wall of the chamber 63 to a source of heating current represented in FIG. 2 by a battery 77 in series with a switch 78. In use, the switch 78 is opened, the valves 67 and 71 set to the first position as shown in FIG. 2 and the pump 7 operated to draw a sample of atmospheric air through the chamber 63.

At least a proportion of any species molecules contained in the sample are adsorbed on the filament 74.

The valves 67 and 71 are then turned to the second position, connecting the chamber 63 into the closed circulatory system described hereinbefore with reference to FIG. 1. After an interval sufficient to ensure that any water vapour from the atmospheric sample which may have been trapped in the chamber is purged therefrom by the gas flow and removed by the filters 16 and 26, the switch 78 is closed to heat the filament. Any species molecules previously adsorbed thereon are consequently desorbed and entrained in the gas flow, which carries them to the detector unit 12.

We claim:

1. Apparatus for detecting trace quantities of a chemical species in a gaseous mixture by drawing the gaseous mixture through a hollow body, said hollow body having serially arranged an inlet, a first, a second and a third internal region and an outlet, the first region containing means for ionising a proportion of the molecules of the gaseous mixture including molecules of the chemical species and means for selecting ions of one polarity for travel with the gaseous mixture into the second region, means for promoting the flow of the gaseous mixture through the second region as a jet of substantially uniform velocity, means for producing in the second region an electric field which urges ions of the selected polarity in a direction opposite to that of the gas flow and means in the third region for collecting ions of the selected polarity, the arrangement being such that, in operation, ions of the selected polarity whose ionic mobilities exceed a value dependent on the strength of said electric field and the velocity of the gas flow can be prevented from entering the third region characterised by means for transferring molecules of the chemical species from the atmosphere to a dry gaseous mixture drawn through the hollow body.

2. Apparatus according to claim 1 in which the transfer means comprises a first chamber having an inlet connected to a source of the dry gaseous mixture and an outlet connected to the inlet of the hollow body, a second chamber having an inlet open to the atmosphere and an outlet connected to pump means for drawing atmospheric air through the second chamber, the first and second chambers being separated by a partition permeable to molecules of the chemical species and substantially impermeable to water molecules.

3. Apparatus according to claim 2 in which the partition is a membrane of a silicone rubber composition.

4. Apparatus according to claim 1 in which the transfer means comprises an elongate chamber having a first port adjacent its one end and a second port adjacent its other end, the chamber containing a filament effective to adsorb molecules of the chemical species when cold and to desorb said molecules when heated, valve means effective in a first position to connect the first port to atmosphere and the second port to pump means for drawing atmospheric air through the chamber and effective in a second position to connect the first port to the inlet of the hollow body and the second port to the source of the dry gaseous mixture, and means for heating the filament when the valve means is in its second position.

5. Apparatus according to claim 1 further characterised by a gas flow circuit such that the dry gaseous mixture, after passing in turn through the transfer means and the hollow body is passed through at least one filter unit of a type effective to remove from the mixture molecules of the chemical species and water molecules and is returned to the transfer means.

6. Apparatus according to claim 5 including a first filter unit, a pump for circulating the gaseous mixture round said gas flow circuit, a flow rate control valve and a second filter unit connected in series between the outlet of the hollow body and the transfer means.

7. Apparatus according to claim 5 in which the dry gaseous mixture is dry air.

8. Apparatus according to claim 5 in which the dry gaseous mixture is an inert gas.

9. Apparatus according to claim 1 in which the means for ionising a proportion of the molecules of the sample is a corona electric discharge having a discharge current no greater than 100 nanoamps.

10. Apparatus according to claim 1 further characterised by means for heating the transfer means to a desired temperature.

11. Apparatus according to claim 1 further characterised by means for heating the hollow body to a desired temperature.

* * * * *